United States Patent [19]

Carlsson et al.

[11] Patent Number: 5,512,306
[45] Date of Patent: Apr. 30, 1996

[54] SMOKING SUBSTITUTE

[75] Inventors: Thommy Carlsson, Helsingborg; Sven B. Andersson, Ödåkra, both of Sweden

[73] Assignee: Pharmica AB, Sweden

[21] Appl. No.: 335,175

[22] Filed: Nov. 7, 1994

Related U.S. Application Data

[63] Continuation of Ser. No. 862,533, Jun. 19, 1992.

[51] Int. Cl.$^6$ .............................. A23G 3/30; A24B 15/00
[52] U.S. Cl. .............................. 426/3; 426/650; 131/347; 131/359; 131/369; 424/434; 424/435; 424/465; 424/489; 424/48
[58] Field of Search ..................... 426/3–6, 650; 131/1, 2, 359, 369, 366, 367

[56] References Cited

U.S. PATENT DOCUMENTS

| | | | |
|---|---|---|---|
| 3,845,217 | 10/1974 | Fernö | 426/3 |
| 3,877,468 | 4/1975 | Lichtneckert et al. | 131/2 |
| 3,901,248 | 8/1975 | Lichtneckert et al. | 131/2 |
| 4,267,166 | 5/1981 | Yajima | 426/3 |
| 4,284,089 | 8/1981 | Ray | 131/270 |
| 4,579,858 | 4/1986 | Fernö et al. | 131/359 |
| 4,655,231 | 4/1987 | Ray et al. | 131/357 |
| 4,967,773 | 11/1990 | Shaw | 424/197.1 |
| 5,055,478 | 10/1991 | Cooper et al. | 426/3 |
| 5,135,753 | 8/1992 | Baker et al. | 424/435 |

FOREIGN PATENT DOCUMENTS

| | | |
|---|---|---|
| 2148749 | 7/1985 | European Pat. Off. . |
| 2275161 | 1/1976 | France . |
| 2608156 | 6/1988 | France . |
| 2142822 | 1/1985 | United Kingdom . |

OTHER PUBLICATIONS

Anal. Chem., 1984, 56:2827–2830.
Chemistry in Britain, 1987, 23:455–458.

Primary Examiner—Jeanette Hunter
Attorney, Agent, or Firm—Pravel, Hewitt, Kimball & Krieger

[57] ABSTRACT

The present invention concerns a smoking substitute composition wherein nicotine is the form of an inclusion complex between nicotine and a cyclodextrincompound.

13 Claims, 1 Drawing Sheet

SMOKING SUBSTITUTE

This is a continuation of application Ser. No. 07/862,533 filed Jun. 19, 1994.

In the U.S. Surgeon General's 1988 report on The Health Consequences of smoking, it was estimated that in the U.S. alone about 300.000 deaths are caused each year by diseases related to cigarette smoking. In fact, excessive smoking is now recognized as one of the major health problems throughout the world. The most advantageous thing a heavy smoker can do is, therefore, to reduce or preferably even stop smoking completely. Experience shows, however, that most smokers find this extremely difficult. It is generally accepted that this difficulty results from the fact that heavy smokers are dependent on nicotine, which is considered to be one of the risk factors in tobacco smoke. The most important risk factors, however, are substances which are formed during the combustion of tobacco, such as carbon monoxide, tar products, aldehydes, and hydrocyanic acid.

One way to reduce smoking is to provide nicotine in a form or manner other than by smoking and some products have been developed to this end. The most successful product, which is used as a smoking substitute and/or as a smoking cessation aid and which is based on nicotine, is the chewing gum Nicorette®. To date this product is the only form of nicotine replacement which has been approved by the Food and Drug Administration (FDA). Nicorette® has been on the market in about thirty countries for several years. In this chewing gum the nicotine is present in the form of a complex with an insoluble cation-exchanger (polacrilex) which is dispersed in a gum base. A buffering agent is also included in this composition. Patents related to this product are the U.S. Pat. Nos. 3,877,468, 3,901,248 and 3,845,217.

Another product within this field is Favor® which was on the U.S. market for approximately 18 months but which had to be withdrawn as it did not fulfil the requirements set up by the Food and Drug Administration. This product, which is covered by the U.S. Pat. Nos. 4,284,089 and 4,800,903, is a nicotine inhalation device consisting of an elongated tube, in which a porous polymer plug including nicotine free base, is arranged. The main problem with this nicotine delivery system concerned the volatility of the nicotine free base which very rapidly disappeared from the system. It has been estimated that the shelf-life of the unrefrigerated vapor inhalor was approximately 1 month.

A product which has not yet been approved by the health authorities but which is now undergoing clinical trials is a nicotine nasal solution of the type disclosed in the U.S. Pat. No. 4,579,858. This product is also based on the use of nicotine free base.

Other compositions for nasal use is disclosed in the U.S. Pat. No. 4,655,231. According to this patent the composition is based on water soluble nicotine salts of organic acids, preferably oxalic acid. To the best of our knowledge no clinical studies have been performed with these compositions. It can be assumed, however, that when the salt dissociates in the nasal cavity, the acid moiety will increase the irritant sensation on the mucous membran originating from the nicotine base formed.

The main problems with products based on nicotine free base originate from the volatility of the nicotine, the irritant sensation of the mucous membranes, and the decomposition of nicotine in the presence of oxygen. To some extent these problems are also met with when nicotine is used in the form of a complex with an insoluble cation-exchanger resin as in the Nicorette® product, which was developed by our company and from which we have by now a broad experience. It should also be born in mind that the nicotine is released from the nicotine resin only after extensive chewing.

The present invention concerns compositions to be used as a smoking substitute and/or as a smoking cessation aid comprising nicotine in the form of an inclusion complex formed between nicotine and a cyclo compound, preferably a cyclized polysaccharide, and a pharmaceutically acceptable carrier or adjuvant.

At present we consider β-cyclodextrin to be the most preferred cyclo compound, but other cyclodextrins such as α- and γ-cyclodextrin can also be used, Also derivatives of cyclodextrines are of interest, e.g. trimethyl-β-cyclodextrin, dimethyl-β-cyclodextrin, hydroxyethyl-β-cyclodextrin and hydroxypropyl-β-cyclodextrin, The compositions of the invention are distinguished by several desirable characteristics making them useful for different types of pharmaceutically acceptable preparations, such as tablets, capsule, powders, chewing gums, These characteristics include improved stability, improved taste, good bioavailability, pH independent release, reduced irritant sensation.

A preferred embodiment of the composition according to the invention is a tablet for sublingual or buccal administration. In this composition the nicotine in the ram of the inclusion complex may be present in an amount of 0.05–10%, and the rest, apart from a minor amount of a conventional lubricant, such as magnesium stearate, is a water-soluble, direct compressible excipient. This excipient should be palatable or tasteless and water soluble and accepted for use in pharmaceutical preparations or as a food additive. With excipients tested so far good results have been obtained with β-cyclodextrin, lactos, sorbitol and mannitol. A special advantage is that this tablet can be very easily prepared with a minimum of additives. Our experiments have shown that the stability of nicotine inclusion complex can be decreased by the addition of common additives and, so far, the best stability results have been obtained with preparations including only the complex, an excipient and a lubricant. Optionally also a flavouring agent could be present. In comparison with the Nicorette® chewing gum it has been found that both the taste and the irritant sensation in the throat are diminished in the sublingual tablet according to the invention. Another interesting finding according to preliminary experiments is that no buffering agent is needed contrary to what could be expected from the experience with the chewing gum, Nicorette®, wherein a buffering agent is necessary.

The cyclodextrin inclusion complexes can be prepared according to methods well known to a person skilled in the art. The most common procedures comprise stirring or shaking of an aqueous solution of the particular cyclodextrin with the nicotine. The reaction is preferably carried out in a common solvent like water. After an equilibrium is reached, the solvent can be removed by filtration. The cyclodextrin-nicotine complex is then mixed with the selected excipients and compressed into tablets or formulated to a powder for nasal administration. It can also be dispersed in a gum-matrix for the preparation of a chewing gum.

Of particular value is the improved stability as stability problems with nicotine pharmaceutical preparations are very usual and difficult to solve. The stability can be divided into three categories:

a) improved stability as regards evaporation (reduced volatility)

b) improved stability as regards decomposition through oxidation (resistance to oxidation) and c) improved stability to light which is related to b) as oxidation of nicotine is believed to take place through radical induced reaction. Such reactions are often catalyzed by light radiation.

According to the invention all these three categories of stability are considerably improved if the complexes according to the invention are used instead of nicotine free base.

When in proper environment (e.g. saliva in the mouth) the inclusion complex of the invention permits release of nicotine. Furthermore, the complexes are easy to handle and can readily be transferred to different pharmaceutical preparations, to which different and desirable release profiles can be imparted.

Figure 1:
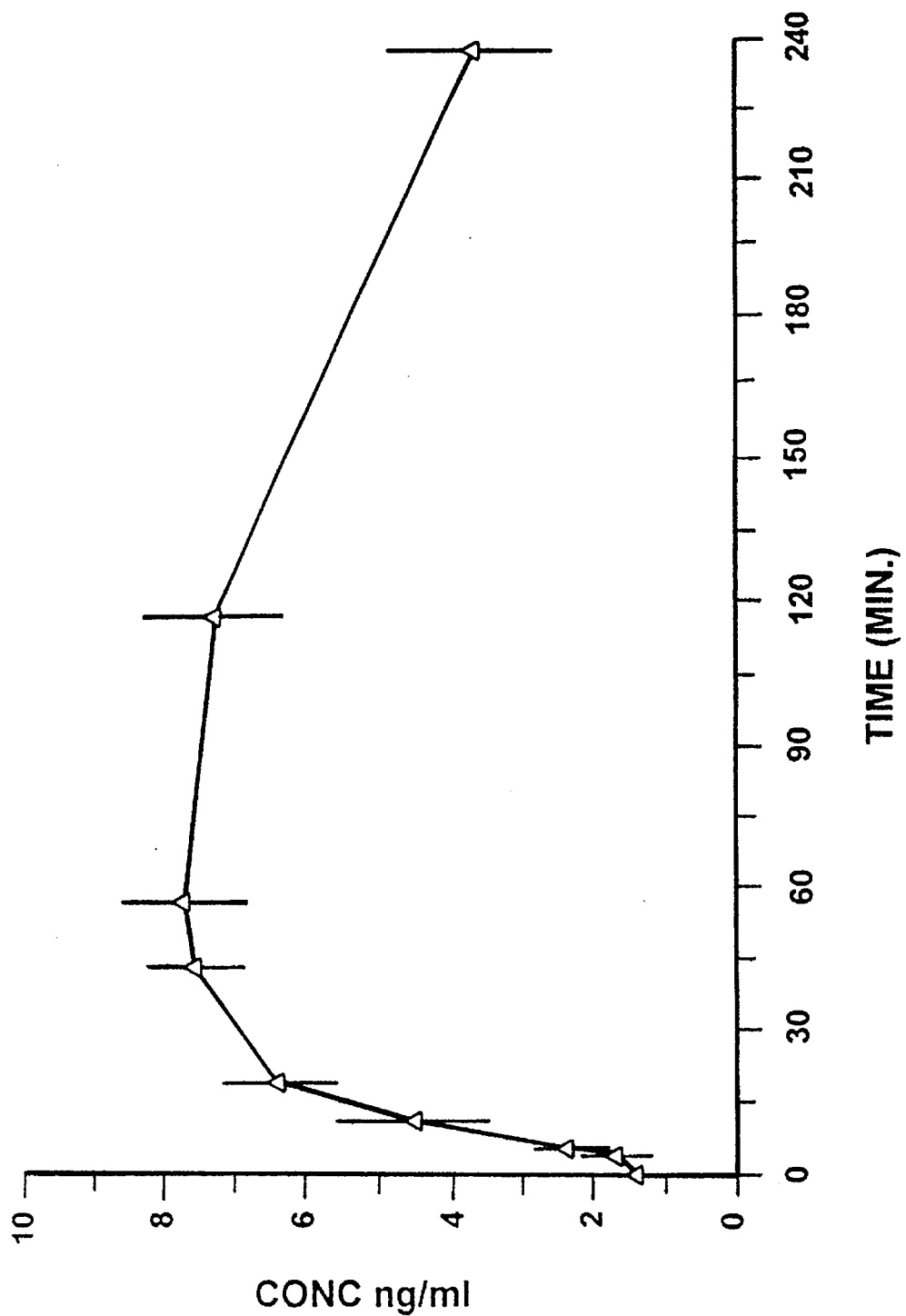
FIG. 1 shows the results of Experiment 2, the average nicotine plasma level of four persons versus time.

The invention is further illustrated by the following examples which should not be construed as limiting the invention:

EXAMPLE 1

Preparation of inclusion complex of β-cyclodextrin (β-CD) and nicotine.

This complex, which is previously known from Anal. Chem. 1984, 56 2827–2830, was prepared as follows:

100 g of water was heated to 75° C., 25 g of β-CD were added and dissolved while stirring the solution. 3,5 ml of nicotine (obtained from Eastman Kodak) were added. The mixture was stirred for about 4 h at ambient temperature. The obtained mixture was filtered and dried in a drying oven at 35° C.

EXAMPLE 2

1.500 tablets having the following composition were prepared.

Composition per tablet:

| β-CD-nicotine | 34,8 mg (respond to 4 mg nicotine) |
| Sorbitol powder | 500 mg |
| PEG 6000 | 100 mg |
| Sodium carbonate | 24 mg |
| Ethyl cellulose N-7 | 12 mg |
| Silicone oil 300/350 cSt | 1,27 mg |

Sorbitol, PEG-6000, β-CD nicotine complex and sodium carbonate were sieved and mixed.

The silicone oil was added to the ethyl cellulose dissolved in ethanol while stirring.

The powder was moistened with the ethanol solution and the obtained product was dried at 40° C. until the ethanol had evaporated and a granulate was obtained. This granulate was sieved and 0,5 % Ng stearate was added. The mixture was agitated for 3 minutes, and compressed to tablets.

EXAMPLE 3

1.500 tablets having the following composition were prepared.

Composition per tablet:

| β-CD-nicotine | 34,8 mg (respond to 4 mg nicotine) |
| Sorbitol powder | 500 mg |
| PEG 6000 | 100 mg |
| Ethyl cellulose N-7 | 12 mg |
| Silicone oil 300/350 cSt | 1,27 mg |

Sorbitol, PEG-6000, β-CD nicotincomplex were sieved and mixed.

The silicone oil was added to the ethyl cellulose dissolved in ethanol while stirring.

The powder was moistened with the ethanol solution and the obtained product was dried at 40° C. until the ethanol had evaporated and a granulate was obtained. This granulate was sieved and 0,5% Mg stearate was added. The mixture was agitated and compressed to tablets.

EXAMPLE 4

Tablets were prepared from the following ingredients:

| β-CD-nicotine | 43,5 g (respond to 2 mg nicotine) |
| β-CD | 179,2 g |
| Mg stearate | 2,3 g |
| 2500 tablets weigh | 225,0 g |

All the ingredients were placed in an environment with low humidity for more than 24 h. The ingredients were sieved through sieve 1,0 and mixed in a double cone mixer for 5 minutes and compressed to tablets.

EXAMPLE 5

Tablets were prepared in essentially the same way as described in Example 4 from the following ingredients:

| β-CD-nicotine | 87,0 g (respond to 2 g nicotine) |
| Lactose | 358,4 g |
| Mg stearate | 4.5 g |
| 5000 tablets weigh | 450,0 g |

EXAMPLE 6

Tablets were prepared in essentially the same way as described in example 4 from the following ingredients:

| β-CD-nicotine | 89,5 g (respond to 2 g nicotine) |
| Sorbitol | 356,0 g |
| Mg stearate | 4,5 g |
| 5000 tablets weigh | 450,0 g |

EXAMPLE 7

Tablets were prepared in essentially the same way as described in example 4 from the following ingredients:

| β-CD-nicotine | 87,0 g (respond to 2 mg nicotine) |
| Starch (Sta Rx 1500) | 358,0 g |
| Mg stearate | 4,5 g |
| 5000 tablets weigh | 450,0 g |

EXAMPLE 8

Tablets were prepared in essentially the same way as described in example 4 from the following ingredients:

| β-CD-nicotine | 89,5 g (respond to 2 g nicotine) |

-continued

| | |
|---|---|
| Mannit | 356,0 g |
| Mg stearate | 4,5 g |
| 5000 tablets weigh | 450,0 g |

EXAMPLE 9

Tablets were prepared in essentially the same way as described in example 4 from the following ingredients:

| | |
|---|---|
| β-CD-nicotine | 87,0 g (respond to 2 mg nicotine) |
| Avicel pH 101 | 358,4 g |
| Mg stearate | 4,5 g |
| 5000 tablets weigh | 450,0 g |

EXPERIMENT 1

Tablets prepared according to the above examples were stored for approximately 1 month in an environment having the temperature 40° C.

The following observations on the tablets were made:
Tablet prepared according to

| Example No | Test time (days) | Appearance |
|---|---|---|
| 2 | 32 | yellow-brown spots |
| 3 | 32 | yellow-brown spots |
| 4 | 32 | without remark |
| 5 | 38 | without remark |
| 7 | 34 | without remark |
| 8 | 34 | without remark |
| 9 | 38 | without remark |

Preliminary results also indicated that the loss of nicotine from the tablets was quite small or neglible. Most nicotine had disappeared from the tablets prepared according to the Examples 2 and 3. No increase of oxidation products of nicotine, such as cotinine, myosmine, nicotine-N-oxide, were found in the tablets after storage for one month at 40° C.

EXPERIMENT 2

In this experiment nicotine-β-cyclodextrin powder was placed in a porous bag of synthetic material (type tea bag) in an amount corresponding to 6 mg nicotine. A bag was placed in the mouth of a person and the nicotine plasma level was measured. FIG. 1 discloses the average nicotine plasma level of four persons versus time.

We claim:

1. A smoking substitute composition for application to the nose or oral cavity, comprising an inclusion complex of nicotine and a cyclized polysaccharide and an excipient acceptable for pharmaceutical use or as a food additive.

2. The composition of claim 1, wherein said cyclized polysaccharide is a cyclodextrin.

3. The composition of claim 9, wherein said cyclodextrin is selected from the group consisting of alphacyclodextrin, gamma-cyclodextrin, beta-cyclodextrin, and derivatives thereof.

4. The composition of claim 3, wherein said cyclodextrine is beta-cyclodextrin.

5. The composition of claim 1 for sublingual or buccal administration, wherein the excipient is a direct compressible, water soluble substance.

6. The composition of claim 1, wherein said excipient is selected from the group consisting of lactose, sorbitol, mannitol, and non-complexed cyclodextrin.

7. The composition of claim 1, further comprising a lubricant.

8. The composition of claim 7, wherein said lubricant is magnesium stearate.

9. The composition of claim 1, in the form of a spray for nasal administration.

10. The composition of claim 1, in the form of a powder.

11. The composition of claim 1, in the form of a tablet.

12. The composition of claim 1, wherein the composition is dispersed in a chewing gum matrix.

13. A composition comprising:
(1) an inclusion complex of nicotine and cyclodextrin, wherein said inclusion complex comprises from about 0.1% w/w to about 10% w/w of said composition;
(2) about 0.5% w/w to about 3% w/w of a lubricant; and
(3) an excipient selected from the group consisting of lactose, non-complexed cyclodextrin, sorbitol, and mannitol.

* * * * *